United States Patent [19]
Williams

[11] Patent Number: 5,110,591
[45] Date of Patent: May 5, 1992

[54] NEEM OIL EMULSIFIER

[75] Inventor: William A. Williams, Latrobe, Pa.

[73] Assignee: PPG Industries, Inc., Pittsburgh, Pa.

[21] Appl. No.: 488,209

[22] Filed: Mar. 1, 1990

[51] Int. Cl.$^5$ ............... A61K 35/78; A61K 31/74; A61K 31/35; A01N 43/16
[52] U.S. Cl. ................. 424/195.1; 424/78; 514/453
[58] Field of Search ............... 424/195.1, 78; 514/453

[56] References Cited

U.S. PATENT DOCUMENTS

| | | | |
|---|---|---|---|
| 4,537,774 | 8/1985 | Shimizu | 424/195.1 |
| 4,556,562 | 12/1985 | Larson | 424/195.1 |
| 4,902,713 | 2/1990 | Rembold | 514/453 |
| 4,943,434 | 7/1990 | Lidert | 424/195.1 |
| 4,946,681 | 8/1990 | Walter | 424/195.1 |

FOREIGN PATENT DOCUMENTS 2082061  3/1982  United Kingdom ............ 424/195.1

OTHER PUBLICATIONS

Kirk-Othmer, Encyclopedia of Chemical Technology, vol. 7, 1979, pp. 146–150, John Wiley & Sons, N.Y.
Feverhare, Dev of a Standardized & Formulated Sep./85 Insecticide, J of Plant. Diseases & Protection 92(6)643–9, Chem Abstracts, 104 19 163705 p (1986).

*Primary Examiner*—Johnnie R. Brown
*Assistant Examiner*—Ralph G. Gitomer
*Attorney, Agent, or Firm*—Irwin M. Stein; Edward J. qhitfield

[57] ABSTRACT

Disclosed are concentrated water-in-oil neem oil emulsions containing a pesticidally effective amount of azadirachtin, which concentrated emulsions, upon dilution with water, form storage stable oil-in-water emulsions.

16 Claims, No Drawings

NEEM OIL EMULSIFIER

BACKGROUND OF THE INVENTION

Due to health and environmental concerns over the use of synthetic pesticides, there is a growing trend toward the use of natural or biorational pesticides which have little or no harmful environmental effects. As disclosed, e.g., in U.S. Pat. No. 4,556,562, one such natural pesticide is azadirachtin which is derived from the seeds of the neem tree (*Azadirachta indica* A. Juss). The neem tree is indigenous to a number of middle and far east countries, e.g., India, Pakistan, Bangladesh, Myanma, Thailand, Malaysia, and parts of Africa.

As described in the aforementioned patent, azadirachtin is typically extracted from the neem seeds along with neem oil which is a triglyceride component also found in neem seeds. The neem oil is reported to protect azadirachtin from ultra-violet degradation.

Neem oil containing the azadirachtin is typically applied to crop seeds or sprayed on the growing crops as an emulsion. Such crop seed or crop treatment deters insects from feeding on the crop, exhibits a growth regulating effect on the insects and interrupts insect propagation. Some insects against which azadirachtin has been found effective include Japanese beetles, fall armyworms, locusts, termites, grasshoppers, tobacco hornworms, tobacco budworms, caterpillars, gypsy moths, rice weevils, aphids, cotton boll moths and the like. Also, azadirachtin-containing neem oil emulsions may be incorporated into insect repellent products, e.g., soaps, sprays, lotions or the like for human or animal use.

However, it is very difficult to form storage stable neem oil emulsions especially when using environmentally safe and acceptable emulsifying agents, i.e., those approved for use as food additives for human consumption under 21 CFR 172 as well as those approved for agricultural use under 40 CFR 180.1001(c),(e).

DESCRIPTION OF THE INVENTION

In its broadest aspect, this invention relates to storage stable, environmentally safe, neem oil emulsions, which emulsions contain a pesticidally effective amount of azadirachtin. Typically, the neem oil as well as the azadirachtin are simultaneously extracted from the seeds of the neem tree. More particularly, this invention provides storage stable, environmentally safe, concentrated water-in-oil microemulsions containing neem oil and a pesticidally effective amount of azadirachtin, which concentrated water-in-oil emulsions, upon dilution with water, form storage stable, environmentally safe, oil-in-water macroemulsions. The emulsions of the invention when coated on crop seeds, sprayed on growing crops or incorporated in soaps, sprays or lotions provide insect repellant properties. For purposes of this invention, microemulsions mean dispersions of very small droplets having a particle size on the order of about 50 nanometers which dispersions from a substantially transparent or translucent system and which form spontaneously when oil and water are mixed with a relatively large amount of surfactant and a cosurfactant. Microemulsions differ from macroemulsions in two respects, namely in their lack of turbidity and their thermodynamic stability.

The concentrated emulsions of the invention contain neem oil, a pesticidally effective amount of azadirachtin, emulsifying agent, polyhydric alcohol and water. Water has been found to be a critical component of the concentrated emulsion, since it has been observed that concentrated neem oil emulsions that do not contain a certain amount of water, ab initio, do not, upon dilution with water to form more workable and handleable systems, form storage stable emulsions. In other words, in order to form a dilute neem oil emulsion by dilution of a concentrated neem oil emulsion, the concentrated emulsion must contain a certain amount of water.

As before mentioned, the neem oil and azadiractin components of the concentrated emulsion of the invention may be extracted from the seeds of the neem tree as described, e.g., in U.S. Pat. No. 4,556,562. Azadirachtin is present in the neem oil/azadirachtin extract in pesticidally effective amount which typically ranges from about 500 to about 5000 parts by weight of azadirachtin per million parts by weight of neem oil.

Emulsifying agents suitable for use in accordance with the invention are preferably nonionic and preferably selected from those approved for food and/or agricultural uses and include, e.g., sorbitan esters, ethoxylated and propoxylated mono- or diglycerides, lactylated mono- or diglycerides, acetylated mono- or diglycerides, citric acid esters of mono- or diglycerides, sugar esters, polysorbates, polygylcerol esters or mixtures thereof. Of the foregoing, polyoxyethylene sorbitan esters (polysorbates) containing from 4 to 20 polyoxyethylene (POE) groups, such as those sold commercially under the trademarks, Tween ® or T-Maz ®, are or mixtures thereof preferred. Some specific examples of preferred POE sorbitan esters include POE (20) sorbitan monooleates, POE (20) sorbitan monolaurate, POE (20) sorbitan monopalmitate, POE (20) sorbitan monostearate, and the like.

Polyhydric alcohols suitable for use in accordance with the invention, some of which are approved for use as food additives, include, e.g., diethylene glycol, triethylene glycol, tetraethylene glycol, glycerol, sorbitol, mannitol, pentaerythritol or mixtures thereof. Straight chain polyhydric alcohols or mixtures thereof containing from 2 to 6 carbon atoms in the chain are preferred and, of these, glycerol is particularly preferred.

In preparing the concentrated emulsions of the invention, the emulsifier system components, i.e., the emulsifying agent, polyhydric alcohol and water, are preferably premixed and blended with the neem oil containing the active pesticide, azadirachtin, although the order of addition is not particularly critical. The concentrated emulsion may contain from about 10 to about 50 parts by weight of emulsifier component and from about 90 to about 50 parts by weight of neem oil/azadirachtin component. Preferably, the concentrated emulsion contains from about 25 to about 50 weight percent of emulsifier component and from about 75 to about 50 weight percent of neem oil/azadirachtin component. The emulsifier component may contain from about 40 to about 60 weight percent of emulsifying agent, from about 20 to about 40 weight percent of polyhydric alcohol and from about 10 to about 25 weight percent of water. Preferably, the emulsifier component contains from about 45 to about 50 weight percent of emulsifying agent, from about 30 to about 35 weight percent of polyhydric alcohol and from about 18 to about 22 weight percent of water. It is, of course, to be understood that the relative amount of each ingredient comprising the emulsifier component is selected so that the weight percentages total 100 percent.

The pH of the concentrated emulsion is not particularly critical, however too alkaline a pH should be avoided so as to minimize the possibility of saponification. The pH of the concentrated emulsion may range from about 2 to 10, and typically ranges from about 5 to 7. Although the concentrated emulsion could be used undiluted, it is somewhat viscous and somewhat difficult to handle and meter so as to assure a uniform, accurate dosage application of active ingredient, i.e., the azadirachtin. In practice the concentrated water-in-oil emulsion is diluted with water, to form a stable oil-in-water emulsion. The extent of dilution, of course, depends on the particular application and may range from as little as one or less part by volume of concentrated emulsion to 99 or more parts by volume of water up to about equal parts by volume of concentrated emulsion and water.

The invention is further illustrated but is not intended to be limited by the following example.

EXAMPLE 5.0 Grams of a clear solution containing 48 percent by weight of T-Maz ® 80K polyoxyethlene (20) sorbitan monooleate, 32 percent by weight of glycerol and 20 percent by weight of deionized water was mixed with 5.0 grams of neem oil containing azadirachtin. The resulting concentrated water-in-oil microemulsion had a pH of 5.7 and a specific gravity of 1.105. 2.0 Grams of the concentrated emulsion was weighed into a 100 milliliter capacity graduated cylinder which was diluted to volume with deionized water. The cylinder was inverted several times to thoroughly mix the contents and allowed to stand quiescent. A stable, uniform oil-in-water macroemulsion resulted.

Although the invention has been described and illustrated in some detail by the foregoing, many variations therein may be made by those skilled in the art without departing from the spirit and scope thereof as defined by the appended claims.

I claim:

1. A concentrated water-in-oil microemulsion which, when diluted with water, forms a storage stable oil-in-water macroemulsion, said concentrated emulsion containing from about 50 to about 90 percent by weight of neem oil containing a pesticidally effective amount of azadirachtin and from about 50 to about 10 percent by weight of an emulsifier composition containing from about 40 to about 60 weight percent of nonionic emulsifying agent selected from the group consisting of sorbitan esters, ethoxylated and propoxylated mono- or diglycerides, lactated mono- or diglycerides, acetylated mono- or diglycerides, sugar-esters polyoxyethylene sorbitan esters containing from 4 to 20 polyoxyethylene groups, polyglycerol esters, or mixtures thereof, from about 20 to about 40 weight percent of polyhydric alcohol containing from 2 to 6 carbon atoms, and from about 10 to about 25 weight percent of water.

2. The microemulsion of claim 1 wherein the polyhydric alcohol is selected from the group consisting of diethylene glycol, triethylene glycol, tetraethylene glycol, glycerol, sorbitol, mannitol, pentaerythritol or mixtures thereof.

3. The concentrated emulsion of claim 1 wherein the emulsifying agent is a polyoxyethylene sorbitan ester or a mixture of polyoxyethylene sorbitan esters containing from 4 to 20 polyoxyethylene groups.

4. The concentrated emulsion of claim 3 wherein the polyoxyethylene sorbitan ester is polyoxyethylene sorbitan monooleate containing 20 polyoxyethylene groups.

5. The concentrated emulsion of claim 1 wherein the polyhydric alcohol is a straight chain polyhydric alcohol containing from 2 to 6 carbon atoms.

6. The concentrated emulsion of claim 5 wherein the polyhydric alcohol is glycerol.

7. The concentrated emulsion of claim 1 wherein the emulsifying agent is polyoxyethylene sorbitan containing 20 polyoxyethylene groups and the polyhydric alcohol is glycerol.

8. The concentrated micro emulsion of claim 1 wherein azadirachtin is present in the neem oil in amount ranging from about 500 to about 5,000 parts by weight per million parts by weight of neem oil.

9. The microemulsion of claim 8 wherein the polyhydric alcohol is selected from the group consisting of diethylene glycol, triethylene glycol, tetraethylene glycol, glycerol, sorbitol, mannitol, pentaerythritol or mixtures thereof.

10. The microemulsion of claim 8 wherein the nonionic emulsifying agent is polyoxyethylene sorbitan ester and the polyhydric alcohol is a straight chain polyhydric alcohol containing from 2 to 6 carbon atoms.

11. The microemulsion of claim 10 wherein the polyoxyethylene sorbitan ester is selected from the group consisting of polyoxyethylene sorbitan monooleate, polyoxyethylene sorbitan monolaurate, polyoxyethylene sorbitan monopalmitate, polyoxyethylene sorbitan monostearate or mixtures thereof, each polyoxyethylene sorbitan ester containing 20 polyoxyethylene groups.

12. The microemulsion of claim 11 wherein the polyhydric alcohol is glycerol.

13. The concentrated microemulsion of claim 8 wherein the concentrated emulsion contains from about 75 to about 50 percent by weight of the neem oil and from about 25 to about 50 percent by weight of the emulsifier composition.

14. The microemulsion of claim 13 wherein the emulsifier composition contains from about 45 to about 50 weight percent of nonionic emulsifying agent, from about 30 to about 35 weight percent of polyhydric alcohol and from 18 to about 22 weight percent water.

15. The microemulsion of claim 14 wherein the polyoxyethylene sorbitan ester is polyoxyethylene sorbitan monooleate, polyoxyethylene sorbitan monolaurate, polyoxyethylene sorbitan monopalmitate, polyoxyethylene sorbitan monostearate or mixtures thereof, each polyoxyethylene sorbitan ester containing 20 polyoxyethylene groups.

16. The microemulsion of claim 15 wherein the polyhydric alcohol is glycerol.

* * * * *

UNITED STATES PATENT AND TRADEMARK OFFICE
CERTIFICATE OF CORRECTION

PATENT NO. : 5,110,591
DATED : May 5, 1992
INVENTOR(S) : William A. Williams

It is certified that error appears in the above-identified patent and that said Letters Patent is hereby corrected as shown below:

Cover page, second column, "qhitfield" should be --Whitfield--.

Column 4, claim 7, line 17, after "sorbitan", add --monooleate--.

Column 4, claim 8, line 20, "micro emulsion" should be --microemulsion--.

Signed and Sealed this

Sixth Day of July, 1993

Attest:

MICHAEL K. KIRK

*Attesting Officer*    Acting Commissioner of Patents and Trademarks